United States Patent [19]

Prescher et al.

[11] 4,059,619

[45] Nov. 22, 1977

[54] PROCESS FOR THE PREPARATION OF PERCARBOXYLIC ACID SOLUTIONS

[75] Inventors: Günter Prescher; Gerd Schreyer, both of Hanau; Otto Weiberg, Neu-Isenburg; Rolf Wirthwein, Hanau; Helmut Waldmenn, Leverkusen; Hermann Seifat, Cologne; Wulf Schwerdtel, Leverkusen; Wolfgang Swodenk, Odenthal, all of Germany

[73] Assignees: Deutsche Gold-und Silber-Scheideanstalt Vormals Roessler, Frankfurt am Main; Bayer Aktiengesellschaft, Leverkusen, both of Germany

[21] Appl. No.: 678,828

[22] Filed: Apr. 28, 1976

[30] Foreign Application Priority Data

Apr. 30, 1975 Germany ............................ 2519289

[51] Int. Cl.$^2$ ...................... C07C 179/10; C01B 15/02
[52] U.S. Cl. ................................ 260/502 R; 423/587; 423/588; 423/589
[58] Field of Search ............................ 203/14, 98, 99; 260/502 R; 423/584, 587, 588, 589

[56] References Cited

U.S. PATENT DOCUMENTS

| | | | |
|---|---|---|---|
| 3,247,244 | 4/1966 | Blumbergs et al. | 260/502 R |
| 3,284,491 | 8/1966 | Korzch et al. | 260/502 R |

FOREIGN PATENT DOCUMENTS

| | | | |
|---|---|---|---|
| 2,262,970 | 11/1974 | Germany | 260/502 R |

*Primary Examiner*—Bernard Helfin
*Assistant Examiner*—W. B. Lone
*Attorney, Agent, or Firm*—Burgess, Dinklage & Sprung

[57] ABSTRACT

Process for continuous production of substantially anhydrous solutions of perpropionic acid in benzene. Aqueous hydrogen peroxide is first reacted with propionic acid in the presence of acid catalyst to form perpropionic acid and water (1). The perpropionic acid is extracted with benzene (5), to provide a benzene phase containing the perpropionic acid (11) and an aqueous raffinate (7). The benzene phase is subjected to an extraction with water (12) involving at least 3 stages, to remove hydrogen peroxide, and the resulting benzene extract (15) is subjected to azeotropic distillation (16) to provide the anhydrous solution (17). The aqueous raffinate, which contains hydrogen peroxide, is distilled to remove water (8) and the resulting concentrate is recycled (2) for use in the reaction (1).

17 Claims, 1 Drawing Figure

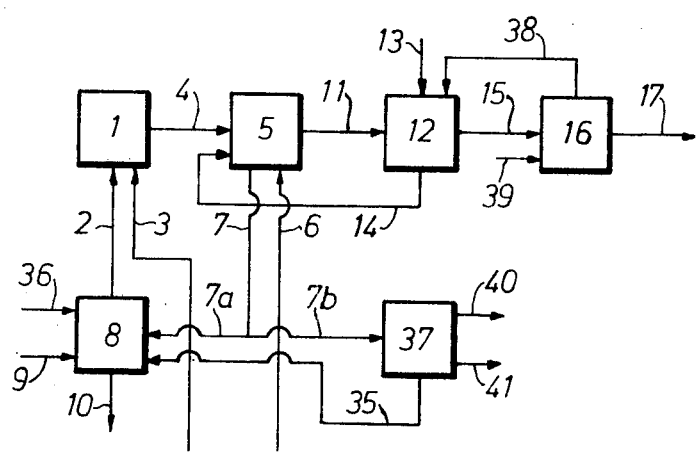

PROCESS FOR THE PREPARATION OF PERCARBOXYLIC ACID SOLUTIONS

The following applications are related to the process hereof for production of propylene oxide as being directed to aspects of the process, some of which are disclosed herein.

| German Serial No. | U.S. Serial No. |
|---|---|
| P 25 19 288.5 | 678,819 |
| P 25 19 300.4 | 678,820 |
| P 25 19 299.8 | 678,821 |
| P 25 19 298.7-42 | 678,822 |
| P 25 19 297.6 | 678,823 |
| P 25 19 295.4 | 678,824 |
| P 25 19 293.2-42 | 678,825 |
| P 25 19 292.1-42 | 678,826 |
| P 25 19 291.0-42 | 678,827 |
| P 25 19 297.4 | 678,829 |

All of the German applications were filed Apr. 30, 1975. Those applications are incorporated herein by reference.

BACKGROUND

The present invention relates to an improved continuous process for the preparation of anhydrous solutions of perpropionic acid in benzene, starting from hydrogen peroxide and propionic acid.

Percarboxylic acids have become increasingly important in the reaction of olefines to give epoxides (D. Swern, "Organic Peroxides", Wiley 1971, Vol. II, page 360 II.) and of cyclic ketones to give lactones (Houben-Weyl "Methoden der organischen Chemie" (Methods of Organic Chemistry) Volume IV/ 2, page 708). However, the aqueous solutions of percarboxylic acids with 2 – 4 carbon atoms, which are readily accessible, for example according to German Patent No. 1,165,576 and German Patent No. 1,170,926, are not suitable for these reactions in all cases due to the presence of water, since water promotes opening of the ring in the products obtained in the reaction. On the other hand, anhydrous solutions of percarboxylic acids give excellent results (see loc. cit.).

The synthesis of anhydrous or substantially anhydrous solutions of percarboxylic acids in organic solvents is known (see Ullmann, Enzyklopadie der Technischen Chemie (Encyclopaedia of Industrial Chemistry), supplementary volume 1970, Neue Verfahren (New Processes), page 181 et. seq. and Swern, Organic Peroxides I, 1970, page 313 et. seq.). These solutions can be obtained, for example, by autoxidation of aldehydes in an anhydrous medium, for example in carboxylic acid esters.

This method has the disadvantage that explosive intermediate products can form in this process and that the carboxylic acid corresponding to the aldehyde is obtained as a by-product after the reaction of the peracid, for example with an olefine.

Organic solutions of percarboxylic acids are also obtained by the reaction of hydrogen peroxide with carboxylic acids in the presence of an acid catalyst, according to equation (1)

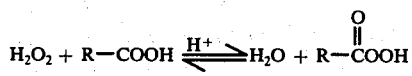
$$H_2O_2 + R-COOH \xrightleftharpoons{H^+} H_2O + R-\overset{O}{\underset{\|}{C}}OOH \quad (1)$$

when the reaction is carried out in the presence of an organic solvent and the water is removed by azeotropic distillation (DTAS (German Published Specification) 1,043,316, U.S. Pat. No. 2,877,266 and DTOS (German Published Specification) 1,917,032).

However, it is also possible first to prepare an anhydrous solution of hydrogen peroxide in an organic solvent and then to react this with a carboxylic acid in the presence of an acid catalyst (DTOS (German Published Specification) 2,038,318).

Furthermore, organic solutions of percarboxylic acids can be prepared by discontinuous or continuous extraction of pure aqueous percarboxylic acid solutions with organic solvents, for example carboxylic acid esters, phosphoric acid esters and chlorinated or aromatic hydrocarbons, and subsequent azeotropic dehydration of the resulting extracts, or also solely by azeotropic dehydration of the aqueous percarboxylic acid solutions. In this case, part of the organic solvent employed is used to dilute the percarboxylic acid (DTOS (German Published Specification) 2,141,155, DTOS (German Published Specification) 2,145,604 and DTOS (German Published Specification) 2,141,156).

Other processes for the preparation of anhydrous solutions of percarboxylic acids are based on the extraction, with organic solvents, of the equilibrium mixture which is set up according to equation (1) and which consists of hydrogen peroxide, carboxylic acid, water and percarboxylic acid and which may still contain the acid catalyst (DTOS (German Published Specification) 2,141,156, DTAS (German Published Specification) 1,048,569 and DTOS (German Published Specification) 1,618,625).

In these processes, the extractions to obtain anhydrous percarboxylic acid solutions are carried out either in several stages or in one stage. In every case the raffinate, which, regarded from the total preparation of the percarboxylic acid, still contained considerable amounts of hydrogen peroxide and possibly of the acid catalyst, was discarded and these substances were thus lost.

However, processes have also been disclosed according to which the raffinates obtained can be worked up in order to recover the amounts of hydrogen peroxide or acid catalysts contained therein and to recycle these to the reaction of hydrogen peroxide with carboxylic acid.

Thus, unreacted hydrogen peroxide contained in the raffinate can be destroyed according to known methods and the acid catalyst can be recovered (DTOS (German Published Specification) 2,312,281).

According to another process, aqueous hydrogen peroxide is first reacted, according to equation (1), with a carboxylic acid with 2 – 4 carbon atoms, in the presence of an acid catalyst, it being possible for the molar ratio of hydrogen peroxide/carboxylic acid employed to be 0.5 – 30 : 1. The reaction mixture is extracted in counter-current with an organic solvent and, if appropriate, the extract, which has been further treated with water, is dehydrated by azeotropic distillation. The raffinate obtained from the extraction of the reaction mixture with an organic solvent contains both unreacted hydrogen peroxide and also the acid catalyst. These can be recovered and recycled into the reaction by feeding the raffinate to an evaporator unit and distilling off, under reduced pressure, the water introduced with the starting materials and formed by the reaction according to equation (1) and recycling the raffinate reconcentrated in this way into the reaction of hydrogen peroxide with the carboxylic acid. In some cases it also suffices to work up only a part of the raffinate in the manner described. The hydrogen peroxide consumed after the reaction according to equation (1) is replenished after reconcentrating the raffinate. According to this process, the yields of percarboxylic acids are 87 - 90.5%, relative to hydrogen peroxide employed (DT-OS (German Published Specification) 2,262,970).

THE INVENTION

The present invention is based on a number of surprising findings in the preparation of solutions of perpropionic acid in benzene by the reaction of hydrogen peroxide with propionic acid, which findings make it possible to carry out the process safely, that is to say under explosion-proof conditions, and lead to a substantial improvement in the yield of perpropionic acid.

The process according to the invention for the continuous preparation of anhydrous solutions of perpropionic acid in benzene by reacting hydrogen peroxide with propionic acid in the presence of sulphuric acid, extracting the reaction mixture with benzene and isolating a substantially anhydrous solution of perpropionic acid as the extract, aftertreating this extract with water and returning the aqueous phase from this after-treatment into the extraction of the reaction mixture, dehydrating the after-treated benzene extract by azeotropic distillation, distilling off water, under reduced pressure, from the total aqueous raffinate from the extraction, recycling the raffinate reconcentrated in this way into the reaction stage and replenishing with amounts of aqueous hydrogen peroxide and propionic acid such that the initial state of the reaction mixture is restored, is characterised in that a. the reaction of hydrogen peroxide with propionic acid in the presence of sulhuric acid is carried out at a molar ratio of hydrogen peroxide : propionic acid employed of 0.8 - 1.4 : 1, the reaction temperature is restricted to a maximum of 60° C and the ratio of hydrogen peroxide (100% by weight) : water by weight before the start of the reaction with propionic acid is restricted to a maximum of 1.2, the concentration of sulphuric acid in the reaction mixture being 10 to 40% by weight, b. the reaction mixture is extracted with benzene in a known manner and the resulting extract is after-treated in at least 3 stages with water or with water containing hydrogen peroxide, the aqueous phase, containing hydrogen peroxide, which is obtained from the azeotropic dehydration of the benzene extract, which is carried out in a known manner, being used, if appropriate with the addition of fresh water, for the treatment in the first stage and the treatment in the second and third stage or in further stages being carried out in countercurrent with fresh water, which enters into the system in the third or final stage and leaves the second stage charged with hydrogen peroxide, the aqueous phases from the first and second stage being recycled into the extraction of the reaction mixture, c. all or part of the amount of aqueous hydrogen peroxide necessary to maintain the reaction, together with all or part of the raffinate which is obtained on extraction of the reaction mixture, is fed direct into the evaporator unit, after which the amount of water introduced in the steady state of the process with the aqueous hydrogen peroxide solution, the amount of water formed during the reaction and the amount of water used for the subsequent extraction are distilled off under reduced pressure, the reconcentration being effected in a rectification unit which consists wholly or partly of tantalum, zirconium a zirconium alloy or a tantalum alloy, with a residence time in the sump of the rectification unit of 3 - 30 minutes and at a sump temperature of 40 - 120° C, and the mixture of hydrogen peroxide, sulphuric acid and water obtained in the sump of this evaporator unit is recycled into the reaction stage (a), and d. part of the raffinate from the extraction of the reaction solution is withdrawn continuously or discontinuously, the hydrogen peroxide contained therein is largely recovered and recycled into the process and the amount of sulphuric acid removed by the withdrawal is replenished.

By means of the combination of the measures according to the invention which are described above, a quite considerable increase in the yield of percarboxylic acid is achieved. In addition, the formation of explosive reaction mixtures is reliably avoided by the measures of the invention according to (a).

Step (a) — production of perpropionic acid

It is known that aqueous hydrogen peroxide, especially in a concentrated form, can form, with organic substances, mixtures which are capable of explosion and which present an explosion hazard. As expected, reaction mixtures such as are formed by the reaction of hydrogen peroxide with propionic acid in the presence of sulphuric acid according to equation (1) are also capable of explosion and present an explosion hazard. Suprisingly, however, it has been found, when the reaction mixtures, under conditions of partial, well-defined enclosure in steel bombs, are exposed to heat and when the reaction mixtures are subjected to the detonation shock of a primer charge whilst enclosed in a steel tube (Explosivstoffe 9, 4 (1961)), that reaction mixtures such as are formed according to equation (1) no longer present an explosion hazard when the molar ratio of hydrogen peroxide : propionic acid employed is restricted to 0.8 to 1.4 : 1, the reaction temperature is restricted to a maximum of 60° C and the ratio of hydrogen peroxide (100% by weight) : water by weight before the start of the reaction with propionic acid is restricted to a maximum of 1.2, the sulphuric acid concentration in the reaction mixture being 10 to 40% by weight. A deviation of the molar ratio employed, for example from 1.3 to 1.5, results in a reaction mixture which, as is shown by the comparison experiment, at 60° C exhibits the properties of a high blasting explosive.

The reaction temperature in the preparation of the reaction mixtures is generally between 20° and 60° C, preferably 30° - 40° C. The starting materials hydrogen peroxide, propionic acid and sulphuric acid are employed in customary commercial concentrations. Hydrogen peroxide is used in aqueous solution in concentrations of 30 - 90% by weight, preferably 50 - 70% by weight. Propionic acid is preferably used in the pure form and sulphuric acid is preferably used as the 95 - 96% strength product.

Step (b) — benzene extraction and water treatment

The reaction mixture is extracted in a known manner with benzene in counter-current. The resulting extract, which contains, in addition to benzene, perpropionic acid, propionic acid, hydrogen peroxide, water and traces of sulphuric acid, is after-treated with water or with water containing hydrogen peroxide in order to separate off the hydrogen peroxide.

The extract generally contains 0.2 to 1% of hydrogen peroxide. The after-treatment is appropriately carried out in suitable extraction apparatuses, specifically employing at least three stages, a mixer-settler being used for the first stage. Further mixer-settlers or other suitable extractors can be used for the following stages. The first stage is preferably treated with the aqueous phase which is obtained from the azeotropic dehydration of the benzene extract and which contains small amounts of hydrogen peroxide, fresh water being added if appropriate. The resulting aqueous raffinate, containing hydrogen peroxide, from the first stage is recycled into the extraction of the reaction mixture. The organic phase from the first stage is extracted in the second and third stage and/or in the further stages in counter-current with fresh water, which enters into the system in the third or final stage and leaves the second stage charged with hydrogen peroxide, this aqueous phase being recycled into the extraction of the reaction mixture.

Both in the first stage and in the final stage, 0.5 to 10% by volume of water or of water containing hydrogen peroxide, relative to the benzene phase, are employed for after-treatment. The ratio of water emanating from the azeotropic dehydration of the benzene extract to fresh water is 1 - 10 : 1 in the first stage. The concentration of hydrogen peroxide in the aqueous phase from the azeotropic dehydration can be 0.5 to 5% by weight. Carrying out the after-treatment according to the process of the invention makes it possible to use the aqueous phase, containing hydrogen peroxide, obtained from the azeotropic dehydration of the benzene extract and thus to recover the hydrogen peroxide container there.

Step (c) — recovery of $H_2O_2$ and acid from the aqueous phase

The raffinate which is obtained from the extraction of the reaction mixture and which essentially consists of water, hydrogen peroxide and sulphuric acid, is reconcentrated in a known manner by distillation (DT-OS (German Published Specification) 2,262,970).

All or part of the amount of aqueous hydrogen peroxide necessary to maintain the reaction, according to the process of the invention is fed together with the total quantity or part of the raffinate from the extraction of the reaction mixture to a rectification unit, which generally consists of a reboiler, a column and a condenser.

Thus, a substantial part of the fresh hydrogen peroxide, which is required in the process, e.g. 50% by weight of this amount, can be added to the raffinate prior to the removal of water by distillation and the remaining 50% by weight of the fresh hydrogen peroxide added to the concentrated raffinate stream.

The process is preferably carried out in such a manner that 50 to 75% by weight of the fresh hydrogen peroxide is added to the raffinate of the extraction prior to concentration, whilst the remaining 25 to 50% by weight of the amount of the fresh hydrogen peroxide needed in the process is added to the raffinate after concentration. It is possible to mix the part of fresh hydrogen peroxide to be added prior to the raffinate concentration with the raffinate before entry into the distillation unit or to introduce both streams separately at a suitable place into the distillation unit. The amount of of fresh hydrogen peroxide, which is not added to the raffinate prior to concentration, can also be introduced directly into the reaction with propionic acid according to (a).

In this case, as in the case of the addition of a part of the fresh hydrogen peroxide to the concentrated raffinate, the concentrations of $H_2O_2$ and acid catalyst must be correspondingly altered in the concentrated raffinate (in so far as the partial streams of fresh hydrogen peroxide which are used in the process as aqueous solutions have the same concentrations).

This alteration to the concentrate must be carried out in order that the required amount ratios of $H_2O_2$, acid catalyst and water be maintained for the reaction with propionic acid. This is expediently carried out in such a manner that the amount of water, which is introduced into the process with the partial stream of the fresh hydrogen peroxide added to the raffinate after concentration or directly to the reaction with propionic acid is removed by distillation; this is preferably achieved in the distillation unit used for the concentration of the raffinate.

It is also possible, however, to introduce partial streams of fresh hydrogen peroxide into the process which have a varying concentration of $H_2O_2$. Thus, it is possible, for example, to add 70% by weight of the required amount of fresh hydrogen peroxide to the raffinate of the extraction prior to concentration in the form of a 50% by weight aqueous solution, whilst the remaining 30% by weight of fresh hydrogen peroxide are introduced as a more highly concentrated aqueous solution of $H_2O_2$, for example, as a 70% by weight solution.

In a preferred embodiment of the process, the process is carried in such a way that the amount of fresh $H_2O_2$, which is added to the raffinate of the extraction prior to removal of water by distillation, amounts to 75 to 95% by weight of the total amount of fresh hydrogen peroxide and that the remaining 5 to 25% by weight of fresh $H_2O_2$ is added to the concentrated raffinate. In a particularly preferred embodiment, the process is so performed that the fresh hydrogen peroxide is introduced by adding the total amount to the raffinate of the extraction prior to concentration in a distillation unit. In the rectification unit, the water formed during the reaction, the water introduced with the hydrogen peroxide and the water used for the after-treatment of the extract is distilled off under reduced pressure.

In place of stainless steels, tantalum, zirconium or a commercially available zirconium or tantalum alloy is used as the material for the whole or part of the rectification unit. In this context tantalum is to be understood as including commercially available sheet tantalum and tantalum alloys as including alloys with zirconium. The zirconium which can be used is, above all, industrial zirconium with a hafnium content of about 1 - 5%. Commercially available zirconium alloys are those with appropriate amounts of tin, iron, chromium and nickel (for example Zircaloy 2 ® or Zircaloy 4 ® ) or alloys with niobium; zirconium is however in general the major component of the alloy.

For further details see S.N. 678,819.

The residence time in the sump of the evaporator unit is restricted to 3–30 minutes and the sump temperature is restricted to 40°–120° C, preferably 60°–85° C. The pressure is 10–250 mm Hg, preferably 50–150 mm Hg.

On prolonged continuous operation of the process, impurities accumulate after a certain time in the aqueous hydrogen peroxide solution, which contains sulphuric acid and which is obtained as the raffinate from the extraction of the reaction mixture, and these impurities promote the decomposition of the perpropionic acid and of the hydrogen peroxide. In order to keep the concentration of the impurities at a constant level it is necessary to withdraw part of the raffinate continuously or discontinuously. The fraction of the raffinate which is withdrawn hourly depends on the loss of active oxygen per unit time and must be determined from case to case. In general, because of the losses of hydrogen peroxide associated therewith, the withdrawn raffinate cannot be discarded. In order to recover the hydrogen peroxide contained in the withdrawn raffinate, this is passed to a recovery unit for hydrogen peroxide. This consists of a pre-heater, a column and a condenser. The distillation column has, in its lower part, a bubble cap tray without a downcomer, so that whilst vapour can flow away into the upper part of the column, the reflux collects on the bubble cap tray. To separate the hydrogen peroxide from the withdrawn solution which contains sulphuric acid, this solution is heated in the pre-heater and fed, below the bubble cap tray without a downcomer, to the column which operates under vacuum. At the same time, steam is passed in at the sump of the column. At the top of the column in the main water condenses and a small reflux is passed to the column. The hydrogen peroxide stripped off is enriched in the upper part of the column and is withdrawn as an aqueous solution from the bubble cap tray without a downcomer. Since the hydrogen peroxide recovered in this way is generally more dilute, for example 10 - 20% strength by weight, than that employed in the process this hydrogen peroxide is recycled to step (c) for reconcentration. The dilute sulphuric acid which collects in the sump of the column is discarded.

The distillation column is operated at a pressure of 25 - 250 mm Hg. The temperature in the pre-heater for the column is 30° - 120° C, preferably 80° - 100° C.

Since with this type of hydrogen peroxide recovery part of the sulphuric acid is lost, this must be replenished. This can be effected either directly by addition into the evaporator unit of step (c) or by addition to the raffinate from the extraction of the reaction mixture upstream or downstream of the evaporator unit. It is also possible to add the amount of sulphuric acid to be replenished to the hydrogen peroxide solution to be fed in before entry into the evaporator unit.

EMBODIMENTS

The present invention is illustrated by the examples which follow and Example 2 indicates the advantages in the use of zirconium over stainless steel in the rectification unit for working up the raffinate.

EXAMPLE 1 (see also FIG. 1)

In continuous operation, 20.12 kg ($\triangleq$ 271 mols) of propionic acid (99.8% strength by weight, product stream 3) and 29.94 kg of an aqueous solution (product stream 2), which on average contains 29.4% by weight of hydrogen peroxide ($\triangleq$ 259 mols), 33.0% by weight of sulphuric acid and 7.5% by weight of Caro's acid, are pumped per hour through the reaction system (1) consisting of a two-stage stirred kettle cascade. The molar ratio of hydrogen peroxide to propionic acid in 1.03 : 1, the hydrogen peroxide bonded in the Caro's acid being calculated as free $H_2O_2$.

With an average residence time of 28 minutes in the stirred kettle cascade and at a reaction temperature of 35° C, 57.4% of the propionic acid is converted to perpropionic acid. The reaction mixture (50.06 kg per hour, product stream 4) contains, on average, 28.0% by weight of perpropionic acid, 17.1% by weight of propionic acid, 7.0% by weight of hydrogen peroxide, 19.7% by weight of sulphuric acid, 4.5% by weight of Caro's acid and 23.7% by weight of water. This reaction mixture is fed, together with the combined aqueous phases (product stream 14) from the extraction unit 12, to the extraction system 5.

A pulsed sieve tray column with 60 trays, a length of 6 m and a diameter of 72 mm is used as the extraction system 5. 45.74 kg per hour of benzene (product stream 6), which contains 0.11% by weight of propionic acid and 0.12% by weight of water, are fed into the column as the extraction agent.

At the upper end of the column, 74.27 kg per hour of benzene extract (product stream 11), which contains, on average, 22.3% by weight of perpropionic acid, 13.8% by weight of propionic acid, 0.54% by weight of hydrogen peroxide, 0.86% by weight of water as well as traces of sulphuric acid, are withdrawn.

The aqueous raffinate from the extraction (product stream 7) is withdrawn at the lower end of the column in an amount of 29.18 kg per hour. This raffinate contains, on average, 11.7% by weight of hydrogen peroxide, 33.8% by weight of sulphuric acid, 7.7% by weight of Caro's acid as well as 0.09% by weight of perpropionic acid and 0.06% by weight of propionic acid.

A small partial stream of the raffinate (product stream 7b) of 0.88 kg/hour ($\triangleq$ 3.0%) is withdrawn and worked up separately.

The bulk of the raffinate (product stream 7a), 28.3 kg/hour, is again made up for renewed reaction with propionic acid by passing it, together with 10.98 kg/hour of 50% strength aqueous hydrogen peroxide ($\triangleq$ 161.4 mols/hour of $H_2O_2$ feed stream 9), a further 0.52 kg/hour of 17 % strength by weight aqueous hydrogen peroxide (product stream 35) and 0.37 kg/hour of sulphuric acid (95.9% strength by weight, stream 36, as replacement for the loss of the $H_2SO_4$ contained in product stream 7b), to a distillation unit 8 and reconcentrating the mixture thus obtained by distilling off water.

The distillation unit 8 consists of a packed column (length = 4 m, diameter = 150 mm), a condenser and a falling film evaporator made of zirconium ("commercial grade"). The mixture of the product streams 7a, 9, 35 and 36 is passed directly to the evaporator. At a pressure of 55 mm Hg, a sump temperature of 76° - 78° C, a temperature at the top of the column of 38° - 39° C, a reflux ratio of 0.55 (reflux/take-off) and with a residence time in the sump of about 12 minutes, 10.21 kg of water are distilled off per hour. This distillate (product stream 10) contains 0.04% by weight of hydrogen peroxide as well as 0.25% by weight of perpropionic acid and 0.16% by weight of propionic acid.

29.94 kg per hour of an aqueous solution (product stream 2), which in turn contains 29.4% by weight of hydrogen peroxide, 33.0% by weight of sulphuric acid and 7.5% by weight of Caro's acid, are withdrawn from the sump of the column. After it has been cooled to 20° C, this mixture is fed back to the reaction system 1.

The raffinate (product stream 7b), 0.88 kg/hour, withdrawn from the aqueous cycle is worked up in a distillation unit (37). This consists of a packed column (length = 4 m diameter = 100 mm), which, above the feedpoint located in the centre, possesses a take-off weir for withdrawing a side stream. The column is operated at a pressure of 50 mm Hg, a temperature at the top of 38° C and a reflux ratio of 0.1.

5.5 kg of steam per hour are blown in above the sump (via line 37a)- 0.52 kg per hour of 17% strength by weight aqueous hydrogen peroxide are withdrawn from the column as a side stream (product stream 35) and fed to the distillation unit 8. In addition, 4.96 kg/hour of water with 0.04% by weight of hydrogen peroxide (product stream 40) are obtained as the distillate and 0.90 kg/hour of an aqueous solution (product stream 41), which contains 1.2% by weight of hydrogen peroxide, 34.7% by weight of sulphuric acid and 5.6% by weight of Caro's acid, are obtained in the sump.

The benzene extract (product stream 11) withdrawn from the extraction column 5 is passed to a further extraction system 12, which is designed as a three-stage battery of mixer-settlers arranged in one plane and each consisting of a mixing pump followed by a separator.

The benzene extract (product stream 11), together with 0.78 kg/hour of fresh water (product stream 13) and 2.92 kg/hour of the aqueous phase (product stream 38) from the azeotropic distillation 16, is fed to the mixing pump of the first stage. The benzene solution, which is withdrawn from the first separator as the light phase, is fed, after passing through the second mixer-settler unit, together with 0.93 kg/hour of fresh water to the mixing pump of the third stage. The aqueous phase separated off in this stage is fed into the second stage.

The aqueous phases obtained in the first stage and the second stage are combined (product stream 14) and passed back, in an amount of 7.65 kg/hour, into the extraction column 5. These combined aqueous phases contain, on average, 3.8% by weight of hydrogen peroxide, 33.7% by weight of perpropionic acid, 21.8% by weight of propionic acid, 10.0% by weight of benzene and a little sulphuric acid. 71.25 kg per hour of a benzene solution (product stream 15), which contains, on average, 19.7% by weight of perpropionic acid, 12.1% by weight of propionic acid, 0.19% by weight of hydrogen peroxide and 4.0% by weight of water, are withdrawn, as the light phase, from the separator of the third stage and fed, together with a solution of a stabiliser, to the azeotropic distillation 16.

A commercially available sodium salt of a partially esterified polyphosphoric acid is used as the stabiliser and is added as a 15% strength by weight solution in propionic acid (0.11 kg/hour, product stream 39).

The distillation unit 16 consists of a packed column (length = 3 m, diameter = 200 mm), a falling film evaporator, a condenser and a separator for phase separation of the distillate at the top of the column. The product stream 15 is fed into the lower part of the column. At a pressure of 300 mm Hg and a temperature at the top of the column of 46° - 48° C, 2.92 kg of aqueous phase and about 54 kg of benzene phase are obtained per hour as the distillate. The benzene phase is returned to the column as reflux, whilst the aqueous phase (product stream 38), which contains 0.82% by weight of hydrogen peroxide, 1.10% by weight of perpropionic acid and 0.34% by weight of propionic acid, is passed into the first stage of the extraction system 12. 68.25 kg per hour of a benzene solution of perpropionic acid (20.49% by weight ≙ 155.2 mols), which also contains 12.67% by weight of propionic acid, 0.16% by weight of hydrogen peroxide, less than 0.1% by weight of water and the abovementioned stabiliser, (product stream 17) are obtained as the sump product from this azeotropic distillation.

The yield of perpropionic acid in the dried benzene solution is 96.1%, relative to the amount of hydrogen peroxide charged to the process (product stream 9).

EXAMPLE 2:

A zirconium tube of the following dimensions was used for the experiment:
11.2 × 1.75 × 700 mm, the volume of the tube was 32.6 cm³. The material had the following composition:

zirconium + hafnium: at least 99.2%
hafnium: maximum 4.5%
iron + chromium: maximum 0.2%.

A mixture of the following composition:
31.5% by weight of hydrogen peroxide,
35.5% by weight of sulphuric acid and
33.0% by weight of water,
was passed through the tube at 80° C, with a residence time of, on average, 30 minutes.

Under the conditions mentioned, an average loss of active oxygen of 0.68%, relative to the charge, was obtained.

Comparison Example

A stainless steel (material No. 1,4571) was used in place of zirconium. The diameter of the tube was 9 mm and the capacity 114 cm³. The mixture employed had the same composition as described above. In this case, however, at 80° C and with a residence time of, on average, 30 minutes, a loss of active oxygen of, on average, 9.5% was obtained.

EXAMPLE

There are various methods for assessing the explosion hazard of materials. For the present invention, the behaviour of the reaction mixtures when exposed to heat under conditions of partial, well-defined enclosure and the behaviour when subjected to the detonation shock of a primer charge were used to assess the explosion hazard of reaction mixtures which are formed by the reaction of hydrogen peroxide with propionic acid in the presence of sulphuric acid.

A method for determining the sensitivity of explosive materials towards exposure to heat, which leads to differentiated, comparable numerical values, is to heat the materials in a steel bomb which is closed off by a nozzle plate with a well-defined orifice. The steel bomb is fabricated from deep-drawing sheet metal and has an internal diameter of 24 mm, a length of 75 mm and a wall thickness of 0.5 mm. At its open end, the bomb is provided with a collar. The bomb is closed by a circular nozzle plate provided with a bore. Nozzle plates having the following diameters for the cylindrical outlet orifice for the gases produced by the decomposition are used: 1; 1.5; 2; 2.5; 3; 3.5; 4; 5; 6; 8; 10; 12; 14; 16 and 20 mm. The materials to be investigated are introduced into the steel bombs and, in order to prevent the initiation of a catalytic decomposition, the walls of the steel bomb can be provided with a coating of polyethylene or the like. The volume of the material sample is about 27 ml. The samples are exposed to heat by supplying heat in an amount of, on average, 2.4 kcals/sec from 4 Teclu-burners. With 3 tests, at least one explosion must take place, the bomb being split into 3 or more parts ("limiting diameter"). The limiting diameter determined in this way is to be regarded as a measure of the heat sensitivity of the material examined. The higher the limiting diameter, the higher is the heat sensitivity. Values of 2 - 2.5 mm are to be regarded as transition values into the dangerous range.

The results of the investigations carried out on the reaction mixtures by the method described above are shown in the table which follows.

In order to obtain further data on the explosion hazard of the reaction mixtures, the behaviour of the reaction mixtures when subjected to the detonation shock of a primer charge, under conditions of enclosure, was investigated. For this purpose about 940 ml of the reaction mixtures were exposed, while enclosed in a 2 inch steel tube, to the detonation shock of a primer charge of 50 g of cyclonite with 5% of wax. In the present case, the conditions were further intensified by the temperature being raised to 60° C and the reaction mixtures being treated with oxygen gas by adding quartz pebbles coated with palladium. Seamless drawn 2 inches steel tubes having a wall thickness of 5 mm and a length of 500 mm and with a welded-on base were used for the experiments. A cap was screwed to the open end and the auxiliary charge was fastened to the inside of the cap. The cap has a bore for the electric fuse with the detonator. This method gives a clear result with regard to the explosibility of a material and it indicates whether the explosion induced was propagated wholly, partly or not at all or whether the tube was disintegrated into splinters. The reaction mixtures tested were prepared from hydrogen peroxide of the indicated concentration using anhydrous propionic acid and concentrated sulphuric acid. The proportion of sulphuric acid was 30% by weight, relative to the mixture of aqueous hydrogen peroxide and propionic acid.

The results of the steel bomb tests and of the 2 inch steel tube tests are given in the table which follows:

the reaction mixture for extraction thereof with benzene, dehydrating the after-treated benzene phase by azeotropic distillation to produce said substantially anhydrous solution of perpropionic acid in benzene and an aqueous phase containing hydrogen peroxide, distilling aqueous raffinate of the benzene extraction under reduced pressure to remove water therefrom and form a concentrated solution of hydrogen peroxide and catalyst, recycling said concentrated solution to said contacting of hydrogen peroxide and propionic acid, and introducing make-up hydrogen peroxide and propionic acid into said contacting step, the improvement which comprises:

a. in said contacting step, the molar ratio of hydrogen peroxide: propionic acid being 0.8 - 1.4 : 1, the reaction temperature being 20°-60° C, the ratio of hydrogen peroxide: water by weight before the start of the reaction thereof with propionic acid based on 100% hydrogen peroxide being up to 1.2, and the concentration of sulfuric acid in the reaction mixture being 10 to 40% by weight;

b. the extraction of the after-treatment being performed in at least three stages by passing the benzene phase serially through the three stages and in each stage extracting with water or water containing hydrogen peroxide, the aqueous phase containing hydrogen peroxide produced in said azeotropic distillation being introduced into the first state, and employed as an extracting agent therein, and aqueous phase containing hydrogen peroxide being withdrawn from the first stage, the extraction in the second and subsequent stages being carried out with fresh water which is introduced into the final stage and is withdrawn from the second stage as an aqueous phase containing hydrogen peroxide, and

| Ratio by weight of hydrogen peroxide : water in the hydrogen peroxide charged | Molar ratio of hydrogen peroxide : propionic acid employed | Steel bomb limiting diameter (mm) | 2"steel tube with primer charge |
|---|---|---|---|
| 1.0 | 0.5 | 1.5 | |
| 1.0 | 0.8 | — | no explosion |
| 1.0 | 1.0 | 2 | no explosion |
| 1.0 | 1.2 | — | no explosion |
| 1.0 | 1.5 | 2.5 | complete explosion |
| 1.22 | 0.8 | 2 | |
| 1.22 | 1.0 | 2 | no explosion |
| 1.22 | 1.2 | 2.5 | no explosion |
| 1.22 | 1.3 | — | no explosion |
| 1.22 | 1.4 | — | complete explosion |
| 1.22 | 1.5 | 4 | |

As can be seen from the table, the range in which there is an explosion hazard is reached when the ratio by weight of hydrogen peroxide : water in the hydrogen peroxide charged is restricted to a maximum of 1.22 but the molar ratio of hydrogen peroxide : propionic acid employed is increased to 1.4–1.5.

What is claimed is:

1. In a process for the continuous production of a substantially anhydrous solution of perpropionic acid in benzene which comprises contacting aqueous hydrogen peroxide with propionic acid in the presence of sulfuric acid as catalyst for the reaction to produce the perpropionic acid and water, extracting the reaction mixture with benzene for formation of a benzene phase rich in perpropionic acid and propionic acid and containing hydrogen peroxide, and an aqueous raffinate phase rich in hydrogen peroxide and catalyst, after-treating said benzene phase by extraction with water for formation of an after-treated benzene phase containing perpropionic acid, propionic acid, water, and a reduced amount of hydrogen peroxide, and aqueous phase containing hydrogen peroxide, recycling said aqueous phase containing hydrogen peroxide to the extraction of recycling the withdrawn aqueous phases from the first and second stages to the extraction of the reaction mixture for extraction thereof with benzene;

c. employing aqueous hydrogen peroxide for the make-up of hydrogen peroxide, introducing at least part of the make-up aqueous hydrogen peroxide and at least part of the aqueous raffinate directly into the raffinate distillation, and in said raffinate distillation distilling off an amount of water about equal to the sum of the water in the aqueous hydrogen peroxide used as said make-up, the water formed during said contacting and the water introduced in said after-treatment, and withdrawing a sump product comprising a mixture of hydrogen peroxide, sulfuric acid, and water and recycling said sump mixture to said contacting, the raffinate distillation being performed in a rectification unit which at least in part consists essentially of a metal of the group tantalum, tantalum alloy, zirconium and zirconium alloy for reduction of decomposition of hydrogen peroxide, the residence time in the sump of the distillation column being 3-30 minutes, and the sump temperature of said raffinate distillation being 40° - 120° C;

d. impurities accumulating in the process, and controlling the level of impurities by withdrawl of impurities from the process.

2. Process of claim 1, wherein, in step (b), the extraction in the second stage and subsequent stages is countercurrent.

3. Process of claim 1, wherein, in step (b), fresh water is employed for the extraction in the first stage, in addition to said aqueous phase from the azeotropic distillation.

4. Process of claim 1, wherein, in step (b), said water or water-containing hydrogen peroxide, in the first stage, and in the subsequent stages, is 0.5-10% by volume of the benzene phase.

5. Process of claim 1, wherein, in step (c), the make-up aqueous hydrogen peroxide distilled in the raffinate distillation is mixed with the aqueous raffinate subjected to the raffinate distillation, before said introduction into the raffinate distillation.

6. Process of claim 1, wherein, in step (c), the raffinate distillation is performed at a pressure of 10-250 mm Hg.

7. Process of claim 1, wherein, in step (c), the raffinate distillation is performed at a pressure of 50-150 mm Hg.

8. Process of claim 1, wherein, in step (c), said metal is industrial zirconium.

9. Process of claim 1, wherein 1, in step (c), said metal is zirconium alloy.

10. Process of claim 1, wherein, in step (c), said metal is industrial zirconium, and the sump temperature is 60°-85° C.

11. Process of claim 1, wherein, in step (d), said withdrawn part is pre-heated and distilled in a distillation unit comprising a column having a bubble cap tray without a downcomer, and a condenser, under reduced pressure to distill aqueous hydrogen peroxide, and recycling the distilled aqueous hydrogen peroxide to step (c).

12. Process of claim 1, wherein, in step (c), at least 50% by weight of the amount of make-up aqueous hydrogen peroxide introduced into the process, is introduced into raffinate distillation.

13. Process of claim 1, wherein, in step (c), 50-75% by weight of the amount of make-up aqueous hydrogen peroxide introduced into the process, is introduced into raffinate distillation.

14. Process of claim 1, wherein, in step (c), 75-95% by weight of the amount of make-up aqueous hydrogen peroxide introduced into the process, is introduced into raffinate distillation.

15. Process of claim 1, wherein, in step (c), all of the make-up aqueous hydrogen peroxide introduced into the process is introduced into the raffinate distillation.

16. Process of claim 1, wherein, in step (b), said water or water-containing hydrogen peroxide, in the first stage, and in the subsequent stages, is 0.5-10% by volume of the benzene phase, and in step (c), the raffinate distillation is performed at a pressure of 10-250 mm Hg.

17. Process of claim 1, wherein, in step (d), for the removal of impurities, a part of the aqueous raffinate or the sump product is withdrawn, and treating said part to recover hydrogen peroxide and produce a sulfuric acid phase, and recycling the recovered hydrogen peroxide for use in said contacting.

* * * * *

UNITED STATES PATENT AND TRADEMARK OFFICE
CERTIFICATE OF CORRECTION

PATENT NO. : 4,059,619
DATED : November 22, 1977
INVENTOR(S) : Günter Prescher et al It is certified that error appears in the above–identified patent and that said Letters Patent are hereby corrected as shown below:

Column 8, line 37, after "(" insert -- $\hat{=}$ --.

Signed and Sealed this

Twenty-third Day of May 1978

[SEAL]

Attest:

RUTH C. MASON
Attesting Officer

LUTRELLE F. PARKER
Acting Commissioner of Patents and Trademarks